United States Patent

Hirschberg et al.

[11] Patent Number: 5,312,440
[45] Date of Patent: May 17, 1994

[54] IMPLANTABLE DEFIBRILLATOR ARRANGEMENT

[75] Inventors: Jakub Hirschberg, Taeby; Hans Anderson, Voellingby, both of Sweden

[73] Assignee: Siemens Aktiengesellschaft, Munich, Fed. Rep. of Germany

[21] Appl. No.: 856,682

[22] Filed: Mar. 24, 1992

[30] Foreign Application Priority Data

Mar. 28, 1991 [JP] Japan .................................. 4110404

[51] Int. Cl.$^5$ ............................................. A61N 1/39
[52] U.S. Cl. ............................................. 607/5
[58] Field of Search ........ 128/419 D, 419 P, 419 PG; 607/4, 5, 34, 36, 37

[56] References Cited

U.S. PATENT DOCUMENTS

| 3,913,588 | 10/1975 | Klomp ............... 128/419 D |
| 4,168,711 | 9/1979 | Cannon, III et al. ........... 128/419 D |
| 4,834,100 | 5/1989 | Charms . | |

FOREIGN PATENT DOCUMENTS

| 0392099 | 10/1990 | European Pat. Off. . |
| 211731 | 11/1971 | Fed. Rep. of Germany . |
| 311116 | 1/1982 | Fed. Rep. of Germany . |

Primary Examiner—Lee S. Cohen
Assistant Examiner—Jeffrey R. Jastrzab
Attorney, Agent, or Firm—Hill, Steadman & Simpson

[57] ABSTRACT

An implantable defibrillator arrangement has a housing adapted for in vivo implantation in a patient, the housing containing a capacitor connectable through a controllable switch arrangement to a voltage source for charging, and two electrodes attached in vivo to the heart. An inductance is also provided for assisting in the generation of an electrical defibrillation pulse, the inductance being contained in a second, separate housing provided with terminals for electrically connecting the inductance via leads to the other housing and to one of the electrodes. The inductance can thereby be easily changed, by connecting an inductance in a second housing having an appropriate value, so as to match the defibrillation pulse to different electrode configuration. It is also possible to provide further passive components in the second, separate housing.

9 Claims, 1 Drawing Sheet

IMPLANTABLE DEFIBRILLATOR ARRANGEMENT

BACKGROUND OF THE INVENTION

1. Field of the Invention

The present invention is directed to an implantable defibrillator arrangement, and in particular such an arrangement making use of a capacitor and an inductance for generating an electrical defibrillation pulse.

2. Description of the Prior Art

In implantable defibrillator arrangments, as exemplified by U.S. Pat. No. 4,834,100, it is conventional to provide a capacitor in an implantable housing, the capacitor being connectable for charging to a voltage source in the housing via a controllable switch arrangement, and also being connectable through an inductance to electrodes arranged in the region of the heart, by means of electrode leads, for generating an electrical defibrillation pulse and supplying the pulse to the heart tissue. In the arrangement disclosed in U.S. Pat. No. 4,834,100, the capacitor is connectable through a controllable switch arrangement either to a voltage source or, in series with an inductance, to two electrode terminals. Electrode leads are connectable outside of the capsule housing to the terminals, the leads terminating in electrodes which are placed at or in the heart of a patient. The capacitor is charged to a prescribed charging voltage as long as the capacitor is connected to the voltage source. For releasing an electrical defibrillation pulse to the heart, the capacitor is briefly connected, via the inductance, to the electrodes by means of switch arrangement, causing a biphase current pulse in the form of a highly attenuated oscillation to be generated. Such a pulse shape has proven particularly effective with respect to the energy required for defibrillation.

The shape of the oscillation is defined by the values of the capacitance of the capacitor, the inductance, and the electrical impedance of the heart tissue between the electrodes. This electrical impedance is substantially dependent on the particular type of electrodes employed, including their shape and their positioning relative to the heart. The defibrillation pulse supplied by this known defibrillator system can therefore significantly deviate from a waveform which is considered optimum, dependent upon which electrodes are employed and on the positions of the electrodes.

SUMMARY OF THE INVENTION

It is an object of the present invention to provide a defibrillator arrangement wherein a defibrillation waveform is generated using a capacitance and an inductance which enables optimization of the defibrillation pulses to be made in a simple manner, even with use of different electrodes and electrode arrangements.

The above object is achieved in accordance with the principles of the present invention in a defibrillator system of the type described above wherein the inductance is contained in a second, separate implantable housing, which is provided with terminals for connecting the inductance in the path of one of the electrode leads. Such a separate housing, containing an inductance selected for generating an optimum defibrillation pulse given the type of electrodes provided for a particular patient and their arrangement at the heart, can be connected at the time of implantation. Such an optimization can also be made in a defibrillator arrangement that has already been implanted, without having to remove the entire arrangement, because replacement of the separate capsule housing containing the inductance is all that is required. The separate housing, because it contains only the inductance, has particularly small outside dimensions and therefore can be implanted at body locations which are easily accessible for later replacement. It is also possible to make use of the separate housing to convert defibrillators designed for generating monophase pulses, whether already implanted or not, into an arrangement which generates biphase defibrillation pulses.

The possibilities for optimizing the defibrillation pulse with respect to different electrodes and electrode arrangements can be further improved in another embodiment of the invention wherein at least one further, passive electrical component is connected between the terminals in the second, separate housing in addition to the inductance. This further component may be a capacitor or a resistor connected either in series or in parallel with the inductance.

In a further embodiment of the invention, the separate housing has at least one additional terminal for a further electrode, and contains at least one additional, passive electrical component which is connected together with the inductance to form a current divider circuit, which divides the defibrillation pulse supplied by the capacitor into different sub-currents for the respective electrodes. Using this arrangement, upon the generation of a defibrillation pulse, the electrical current density is distributed in the heart muscle in a manner adapted to the arrangement (positioning) of the electrodes and thus be distributed so that the current can penetrate the thickest zones of the heart muscle, which form the main portion of the heart muscle mass, in order to achieve reliable defibrillation. Again, existing defibrillators, implanted or otherwise, which are designed only for the connection of two electrodes can be correspondingly retrofitted.

As noted above, the second, separate housing can have relatively small exterior dimensions, and therefore it is subject to far fewer limitations as to the implantation location in the human body than the main (first) capsule housing, which contains the voltage source and the capacitor. In a further embodiment of the defibrillator arrangement of the invention, the separate housing has a surface with at least regions thereof which are electrically conductive, the surface (or regions thereof) functioning as one of the electrodes of the defibrillator arrangement. The second, separate housing can then be implanted at or in the proximity of the heart and additionally assumes the function of a defibrillator electrode.

A plurality of such second, separate housings, each having an inductance of a different value therein, or further combinations of passive electrical components in addition to the inductance, can be provided to the physician to expand his or her choices for selecting an inductance or component combination best suited to the particular electrode arrangement being employed at the time.

DESCRIPTION OF THE PREFERRED EMBODIMENTS

Figure 1:
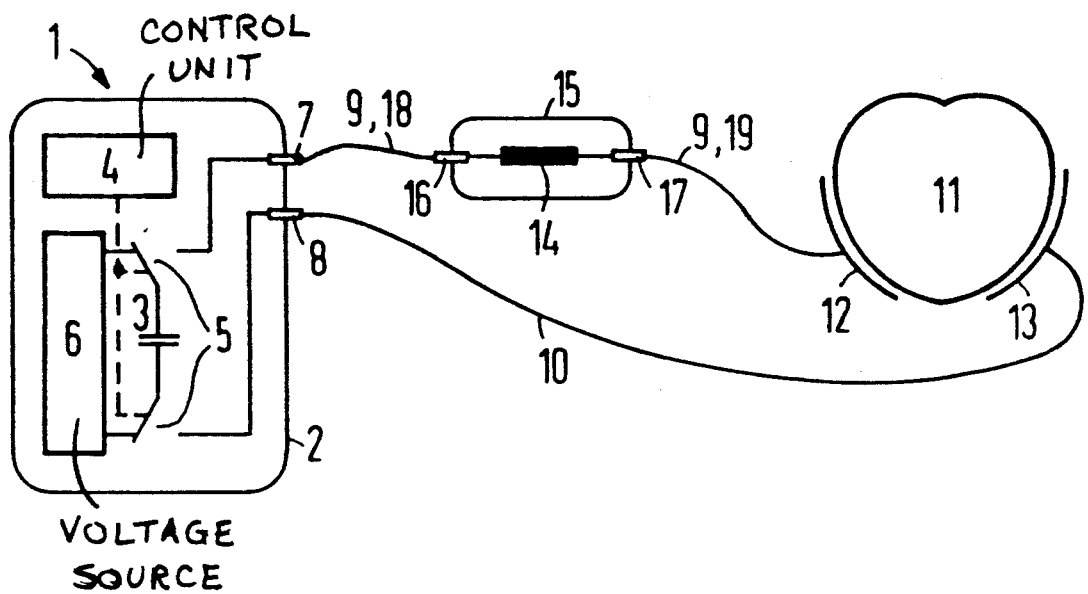
FIG. 1 is a schematic diagram of a first embodiment of a defibrillator arrangement having first and second housings, constructed in accordance with the principles of the present invention.

An implantable defibrillator 1 is shown in FIG. 1, the defibrillator 1 being of the conventional type for generating monophase defibrillation pulses. The defibrillator 1 includes a capsule housing 2, adapted for in vivo implantation in a patient, containing a capacitor 3. The capacitor 3 is connected via a switch arrangement 5, controllable by a control unit 4, either to a voltage source 6 or to two externally accessible electrode terminals 7 and 8. The electrode terminals 7 and 8 are connected via electrode leads 9 and 10 to two electrodes 12 and 13 placed at a heart 11. An inductance 14 is connected in the path of the electrode lead 9, the inductance 14 being contained in a second, separate housing 15. The housing 15 has a terminal 16 which is connected via a first section 18 of the electrode 9 to the output terminal 7 of the defibrillator 1. The housing 15 also has a terminal 17 which is connected via a second section 19 of the electrode lead 9 to the electrode 12.

The housings 2 and 15 each consist of tissue-compatible material, for example titanium, and the terminals 7, 8, 16 and 17 are in the form of insulated bushings extending through the metal housing. The separate housing 15, however, may alternatively consist of plastic, for example silicone, in order to more simply integrate the housing 15 into the electrode lead 9. The housing 15 may have a shape other than shown in the drawing, to facilitate implantability.

As long as the capacitor 3 is connected to the voltage source 6 via the switch arrangement 5, it will be charged to a prescribed charging voltage. For releasing an electrical defibrillation pulse to the heart 11, the capacitor 3 is briefly connected by the switch arrangement 5 to the electrodes 12 and 13 via the inductance 14. This causes the generation of a biphase current pulse in the form of a highly attenuated oscillation. The shape of the current pulse is defined by the values for the capacitance of the capacitor 3, the inductance 14, and the impedance of the heart tissue between the electrodes 12 and 13. Because the value for the impedance of the heart tissue between the electrodes 12 and 13 changed dependent on the size and arrangement of the electrodes at the heart 11, the defibrillation pulse supplied to the heart 11 can deviate from a pulse shape which is considered optimum with respect to defibrillation effectiveness. This deviation can be counteracted in a simple manner by selecting a suitable value for the inductance 14, so that the second, separate housing 15 having the selected inductance 14 must merely be initially implanted together with the defibrillator 1, or can be implanted in a patient as a replacement, or addition to, an existing defibrillator arrangement. Because the separate housing 15 can have relatively small dimensions, it can be implanted at a location in the body which is easily accessible for replacement.

For further optimization of the defibrillation pulse, a further, passive electrical component (not shown in FIG. 1) in the form of a resistor or a capacitor can be provided in the second separate housing 15, in addition to the inductance 14. This further, passive electrical component can be connected either in series with the inductance 14 or in parallel with the inductance 14 between the terminals 16 and 17. This is shown below in FIG. 3 in an exemplary embodiment.

Figure 2:
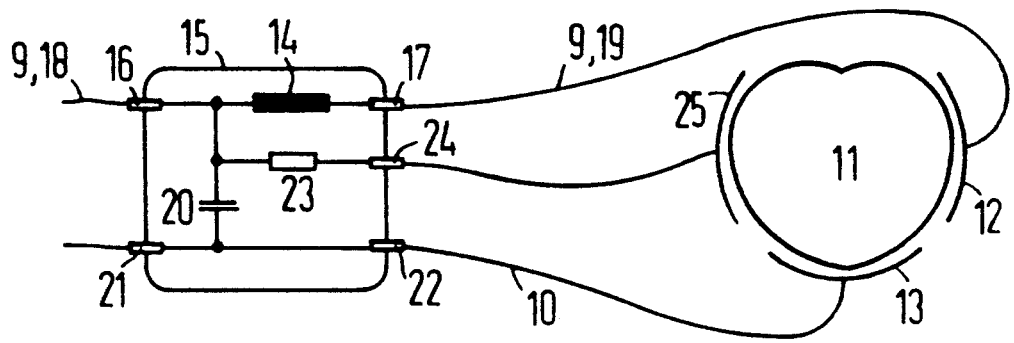
FIG. 2 is a schematic diagram showing a further embodiment of a current divider circuit in the second housing in portion of a defibrillator arrangement constructed in accordance with the principles of the present invention.

As shown in FIG. 2, the further, passive electrical component 20 (a capacitor in this case) can be arranged between the electrode leads 9 and 10, for which purpose the second, separate housing 15 is provided with further terminals 21 and 22 for the electrode lead 10. Moreover, the separate housing 15 shown in FIG. 2 contains an additional, passive electrical component 23 (in the form of a resistor) which is connected at a one side to the terminal 16 connected via the lead section 18 to the defibrillator 1 (not shown in FIG. 2). The other side of the component 23 is connected to an additional terminal 24 for a further electrode 25 placed at the heart 11. This arrangement achieves, when generating a defibrillation pulse, a distribution of the electrical current density in the heart muscle according to the arrangement of the electrodes 12, 13 and 25 and dependent on the values for the components 14, 20 and 23. The current density is preferably distributed so that current penetrates the thickest zones of the heart muscle which form the main part of the heart muscle mass in order to achieve reliable defibrillation.

Figure 3:
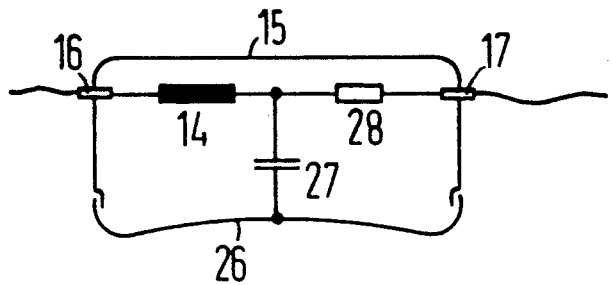
FIG. 3 is a schematic diagram of a third embodiment of a second housing forming an electrode, in a portion of a defibrillator arrangement constructed in accordance with the principles of the present invention.

An exemplary embodiment is shown in FIG. 3 of the second, separate housing 15 wherein a region 26 of the housing surface is fashioned as an electrode, by virtue of being connected via a capacitor 27 to a voltage tap of a series circuit consisting of the inductance 14 and a resistor 28, which is disposed between the terminals 16 and 17. The use of the housing 15, with the aforementioned region 26, as one electrode of the defibrillator arrangement is facilitated by the small dimensions of the housing 15, which permit the housing 15 to be placed in or near the heart without difficulty.

The exemplary embodiments show the structure of the separate housing 15 in schematic illustrations. The housing shape can be altered dependent on the implantation location in the body of the patient, as may be considered preferable.

Lastly, the illustrated selection and arrangement of the passive components 14, 20, 23, 27 and 28 are considered only as examples among a plurality of further possible combinations.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable defibrillator system comprising:
    a first housing for in vivo implantation in a patient;
    at least two leads, each terminating in an electrode, for in vivo implantation in the region of the heart of said patient;
    a capacitor and a voltage source contained in said first housing;
    switching means contained in said first housing for selectively connecting said capacitor to said voltage source to charge said capacitor and for connecting said capacitor across said electrodes of said leads for supplying a defibrillation pulse via a current path including said leads to said heart; and a second housing mechanically connected to one of said leads, for in vivo implantation in said patient, containing an inductance electrically connected in said current path.

2. An implantable defibrillator system as claimed in claim 1, wherein said second housing has first and second terminals between which said inductance is electrically connected, and further comprising at least one additional electrical component electrically connected between said terminals in said second housing.

3. An implantable defibrillator system as claimed in claim 2 further comprising a set containing a plurality of housings from which said second housing is selectable, each housing in said set containing a different combination of an inductance and a passive electrical component.

4. An implantable defibrillator system as claimed in claim 1 wherein said second housing has a surface with at least a region thereof consisting of electrically conductive material, said region of said surface of said second housing forming a defibrillation electrode for said defibrillator system.

5. An implantable defibrillator system as claimed in claim 1 further comprising a set containing a plurality of housings from which said second housing is selectable, each housing in said set containing an inductance having a different value.

6. An implantable defibrillator system as claimed in claim 1 wherein said second housing has first and second terminals between which said inductance is connected with one of said two leads being connected to said second terminal, and third and fourth terminals with the other of said two leads being connected to said fourth terminal, said capacitor being connected across said first and third terminals, and a passive electrical component in said second housing connected between said inductance and said fourth terminal and forming, in combination with said inductance, current distribution means for dividing current in said defibrillation pulse between the respective electrodes of said two leads.

7. An implantable defibrillator system as claimed in claim 6 wherein said second housing has a fifth terminal, said system further comprising a third lead connected to said fifth terminal and terminating in an electrode for in vivo implantation in the region of the heart of said patient, and a further passive electrical component in said second housing connected between said inductance and said fifth terminal and forming, in combination with said inductance and said passive electrical component, current distribution means for dividing current in said defibrillation pulse among the respective electrodes of said first, second and third leads.

8. An implantable defibrillator system comprising:
a first housing for in vivo implantation in a patient;
a plurality of leads, each terminating in an electrode, for in vivo implantation in the region of the heart of said patient;
a capacitor and a voltage source contained in said first housing;
switching means contained in said first housing for selectively connecting said capacitor to said voltage source to charge said capacitor or for connecting said capacitor across two output terminals of said first housing; and
a second housing for in vivo implantation in said patient; separate from said first housing, having two inputs respectively connected to said two output terminals of said first housing, and having a plurality of outputs respectively connected to said plurality of leads, said second housing containing current distribution means for dividing current contained in a defibrillation pulse generated by said capacitor among said plurality of leads.

9. An implantable defibrillator system comprising:
electrical means for generating a defibrillation pulse having a waveform of a selected configuration, said electrical means including first and second electrical components each of which contributes to said configuration of said waveform.
a first housing for in vivo implantation in a patient containing said first electrical component;
a second housing for in vivo implantation in said patient containing said second electrical component;
conductor means extending between said first and second housings for electrically connecting said first and second electrical components; and
electrode means connected to one of said first or second housings for supplying said defibrillation pulse to the heart of said patient.

* * * * *